United States Patent
Suda et al.

(10) Patent No.: US 7,473,298 B2
(45) Date of Patent: Jan. 6, 2009

(54) CHARGED WATER PARTICLE, AND METHOD FOR CREATING ENVIRONMENT WHERE MIST OF CHARGED WATER PARTICLE IS DISPERSED

(75) Inventors: Hiroshi Suda, Takatsuki (JP); Yasunori Matsui, Hikone (JP); Narimasa Iwamoto, Nabari (JP); Toshiyuki Yamauchi, Ibaraki (JP); Shigekazu Azukizawa, Hikone (JP); Takayuki Nakada, Hikone (JP); Tomonori Tanaka, Kasugai (JP); Tomohiro Yamaguchi, Yasu (JP)

(73) Assignee: Panasonic Electric Works, Co., Ltd., Osaka (JP)

( * ) Notice: Subject to any disclaimer, the term of this patent is extended or adjusted under 35 U.S.C. 154(b) by 379 days.

(21) Appl. No.: 10/552,743

(22) PCT Filed: May 26, 2004

(86) PCT No.: PCT/JP2004/007593
§ 371 (c)(1),
(2), (4) Date: Oct. 12, 2005

(87) PCT Pub. No.: WO2004/105958
PCT Pub. Date: Dec. 9, 2004

(65) Prior Publication Data
US 2006/0214020 A1    Sep. 28, 2006

(30) Foreign Application Priority Data
May 27, 2003  (JP) .............................. 2003-149807
Dec. 22, 2003  (JP) .............................. 2003-425862

(51) Int. Cl.
*B03C 3/013* (2006.01)

(52) U.S. Cl. ........................ 95/64; 95/65; 95/71; 96/27; 96/53; 239/3; 239/695; 239/696

(58) Field of Classification Search .................... 96/27, 96/52, 53, 50, 44, 46, 47; 95/64–66, 71, 95/75; 239/3, 690, 695–698, 704, 706
See application file for complete search history.

(56) References Cited

U.S. PATENT DOCUMENTS 3,503,704 A * 3/1970 Marks ........................ 423/212

(Continued)

FOREIGN PATENT DOCUMENTS

EP      1 146 057       10/2001

(Continued)

OTHER PUBLICATIONS

Hawley, Gessner G.; "The Condensed Chemical Dictionary"; 1971; Eighth Edition; Van Nostrand Reinhold Company; pp. 171, 455, 456, 671, 751, 802.*

(Continued)

*Primary Examiner*—Richard L Chiesa
(74) *Attorney, Agent, or Firm*—Greenblum & Bernstein, P.L.C.

(57) ABSTRACT

Charged fine particulate water is provided, which has a nanometer particle size, for example, a particle size of 3 to 100 nm, and contains radicals such as hydroxyl radicals and superoxides. This charged fine particulate water can be generated by applying an electric-field intensity of 700 to 1200 V/mm between a pair of electrodes, while supplying water between the electrodes. By allowing the thus obtained charged fine particulate water to diffuse into an indoor space, it is possible to effectively remove bad odor components/bacteria from the indoor space.

6 Claims, 5 Drawing Sheets

U.S. PATENT DOCUMENTS

| | | | |
|---|---|---|---|
| 3,807,137 A * | 4/1974 | Romell | 95/72 |
| 3,926,586 A * | 12/1975 | Matts | 95/72 |
| 3,958,959 A * | 5/1976 | Cohen et al. | 95/64 |
| 3,960,505 A * | 6/1976 | Marks | 422/168 |
| 4,095,962 A * | 6/1978 | Richards | 95/65 |
| 4,146,371 A * | 3/1979 | Melcher et al. | 95/62 |
| 4,380,786 A * | 4/1983 | Kelly | 361/228 |
| 4,581,675 A * | 4/1986 | Kelly | 361/228 |
| 4,680,163 A | 7/1987 | Blidschun et al. | |
| 4,696,719 A * | 9/1987 | Bischoff | 202/205 |
| 4,979,968 A * | 12/1990 | Jido | 96/27 |
| 5,196,171 A * | 3/1993 | Peltier | 422/121 |
| 5,213,595 A * | 5/1993 | Kim | 96/27 |
| 5,337,963 A | 8/1994 | Noakes | 239/690 |
| 5,503,335 A * | 4/1996 | Noakes et al. | 239/690 |
| 5,523,566 A * | 6/1996 | Fuerstenau et al. | 250/282 |
| 5,873,523 A * | 2/1999 | Gomez et al. | 239/3 |
| 5,914,454 A * | 6/1999 | Imbaro et al. | 95/64 |
| 5,935,538 A * | 8/1999 | Tabatabaie-Raissi et al. | 423/215.5 |
| 5,968,231 A * | 10/1999 | Parmentier et al. | 95/28 |
| 6,471,753 B1 * | 10/2002 | Ahn et al. | 96/27 |
| 6,555,611 B2 | 4/2003 | Tachifuji et al. | 524/451 |
| 6,764,720 B2 * | 7/2004 | Pui et al. | 427/479 |
| 7,247,338 B2 * | 7/2007 | Pui et al. | 427/2.24 |
| 2002/0007869 A1 * | 1/2002 | Pui et al. | 141/173 |
| 2003/0143315 A1 * | 7/2003 | Pui et al. | 427/2.1 |
| 2005/0116070 A1 * | 6/2005 | Ganan Calvo et al. | 239/706 |
| 2006/0214020 A1 * | 9/2006 | Suda et al. | 239/3 |

FOREIGN PATENT DOCUMENTS

| | | |
|---|---|---|
| JP | 53-141167 | 12/1978 |
| JP | 62-144744 | 6/1987 |
| JP | 2001-96190 | 4/2001 |
| JP | 2001-170514 | 6/2001 |
| JP | 3260150 | 12/2001 |
| JP | 2002-203657 | 7/2002 |
| JP | 2003-14261 | 1/2003 |
| JP | 2003-79714 | 3/2003 |
| WO | 01/68242 | 9/2001 |
| WO | 02/30163 | 4/2002 |

OTHER PUBLICATIONS

English Language Abstract of JP 2001-170514.
English Language Abstract of JP 62-144744.
English Language Abstract of JP 2002-203657.
English Language Abstract of JP 2001-96190.
English Language Abstract of JP 53-141167.
English Language Abstract of JP 2003-79714.
English Language Abstract of JP 2003-14261.

* cited by examiner

CHARGED WATER PARTICLE, AND METHOD FOR CREATING ENVIRONMENT WHERE MIST OF CHARGED WATER PARTICLE IS DISPERSED

CROSS-REFERENCE TO RELEVANT APPLICATIONS

This Application is a U.S. National Stage Application of International Patent Application No. PCT/JP2004/007593, filed on May 26, 2004.

TECHNICAL FIELD

The present invention relates to charged fine particulate water, and a method of creating an environment where the mist of charged fine particulate water is dispersed.

BACKGROUND ART

Japanese Patent Early Publication [kokai] No. 2001-170514 discloses that charged fine particulate water generated by applying electric charges to water is used as an effective dust collector due to the high adsorption property in the air.

On the other hand, it is known that radicals are active chemical species, and excellent in decomposing/deodorizing bad-odor components due to their high chemical reactivity. However, since the radicals are unstable in the air, so that the lifetime is short, they often disappear before reacting with the bad-odor components. From this reason, it has been difficult to sufficiently obtain the effect of the radicals.

In addition, Japanese Patent Early Publication [kokai] No. 53-141167 or No. 2001-96190 discloses cleaning the air by use of fine particulate water containing radicals. However, since the charged fine particulate water has a micrometer particle size, it is hard to diffuse in a space. Therefore, the effect of deodorizing/eliminating the bad-odor components/bacteria adhered to a curtain, clothes and wall surfaces spaced by some distance in a room is not still enough.

SUMMARY OF THE INVENTION

In consideration of the above-described problems, a primary concern of the present invention is to provide charged fine particulate water characterized by having a nanometer particle size and containing radicals.

According to the charged fine particulate water of the present invention, the lifetime of chemically unstable radicals is increased by containing the radicals in the charged fine particulate water having the nanometer particle size, and the diffusion property of the charged fine particulate water into a room is improved. Therefore, bad-odor components adhered to a curtain, clothes and wall surfaces in the room can be effectively deodorized. In addition, it is possible to effectively inactivate bacteria, mold fungus, viruses, and allergens such as pollen, and improve the moisture retention of skin.

A further concern of the present invention is to provide a method of creating an environment where a mist of charged fine particulate water is dispersed. This method comprises the steps of:

providing a pair of electrodes, water supply unit configured to supply water between the electrodes, and a voltage applying unit configured to apply a voltage between the electrodes;

generating the mist of charged fine particulate water having a particle size of 3 to 100 nm and containing radicals by applying a high voltage between the electrodes, while supplying water between the electrodes with the water supply unit; and supplying the mist into a desired space to create the environment where the mist of the charged fine particulate water is dispersed in the desired space.

According to this method, it is possible to stably achieve the space, in which the charged fine particulate water having a relatively uniform particle size in the range of 3 to 100 nm is distributed.

Additional features of the present invention and advantages brought thereby will become more apparent from the best mode for carrying out the invention described below.

BEST MODE FOR CARRYING OUT THE INVENTION

Charged fine particulate water of the present invention and the generation method are explained according to preferred embodiments, referring to the attached drawings.

Figures 1A, 1B:
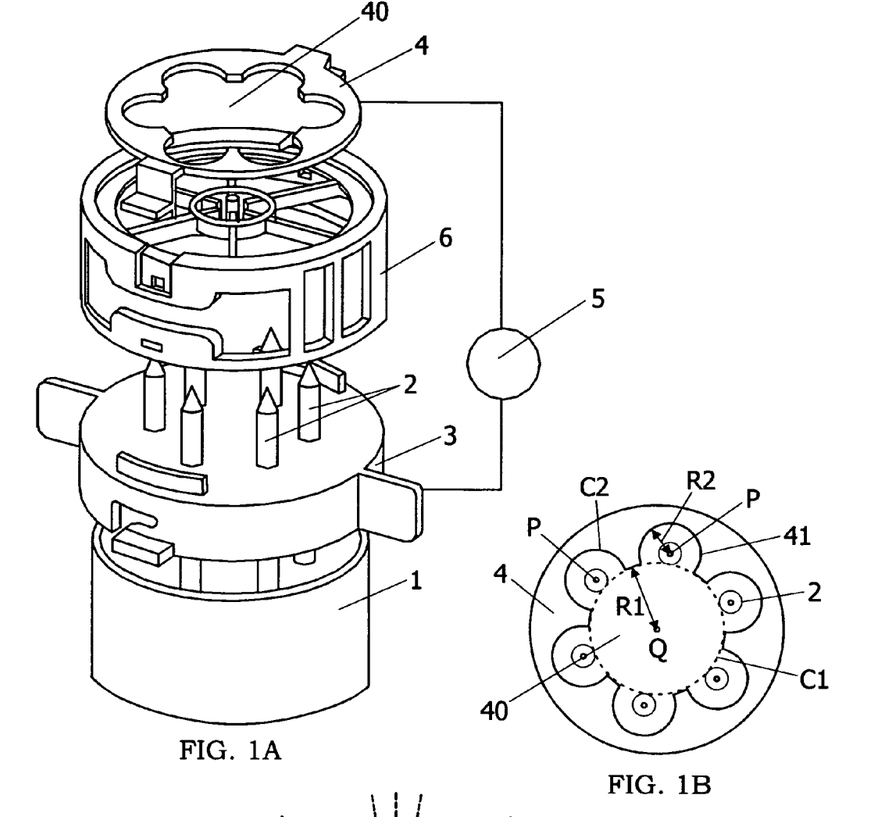
FIGS. 1A and 1B are an exploded perspective view and a top view of an apparatus for generating charged fine particulate water of the present invention.

The charged fine particulate water of this embodiment can be generated by preparing a pair of electrodes, water supply means configured to supply water between the electrodes, and a voltage applying unit configured to apply a voltage therebetween, and applying a high voltage between the electrodes, while supplying water between the electrodes by the water supply unit. Specifically, as shown in FIG. 1A, it is preferred to use an electrostatic atomizer composed of a water tank 1, a plurality of water transfer members 2, each of which is configured in a rod shape having a bottom end, which can contact water in the water vessel 1, first electrode 3 used to support the water transfer member 2 and apply the voltage to water, second electrode 4 disposed at a position facing top ends of the water transfer members 2, and the voltage applying unit 5 for applying the high voltage between the first and second electrodes (3, 4).

The water transfer member 2 used as the water supply means is made of a porous material, and has the capability of sucking up water in the water tank 1 from the bottom end toward the top end by capillary phenomenon. To stably transfer water by the capillary phenomenon, and generate the charged fine particulate water having a uniform particle size, it is preferred to use a porous ceramic material, particularly the porous ceramic material having a porosity of 10 to 60% and a grain size of 1 to 100 µm. Alternatively, a felt and so on may be used. The top end of the water transfer member 2 is of a needle shape. For example, it is preferred that a diameter of the needle end is φ0.5 mm or less. In addition, it is preferred that the water transfer members 2 are evenly spaced from each other on the circumference of a circle, which has a center corresponding to a center of the first electrode 3, and the water transfer members 2 are supported by the first electrode 3 so as to project from a top surface of the first electrode 3 at a required height. In the electrostatic atomizer of the drawings, six water transfer members 2 are disposed at vertices of a regular hexagon.

The second electrode 4 having an opening 40 at its center is attached to the first electrode 3 through a tubular member 6 made of an electrically insulating material. Therefore, the charged fine particulate water is generated in an internal space of the tubular member 6, and then provided to the outside through the opening 40. In this embodiment, as shown in FIG. 1B, the opening 40 has a shape configured by synthesizing a large circular opening C1 having a center Q and a radius R1, with small circular openings C2 each having a center P and a radius R2. In the figure, the number of the small circular openings C2 is six. The centers P of the small circular openings C2 are evenly positioned on the circumference of a circle in a concentric relation with the large circular opening C1. The needle end of each of the water transfer members 2 is positioned at the center P of the small circular opening C2. Therefore, an edge portion 41 of the second electrode 4 facing the respective circular opening C2 is spaced by the distance R2 from the needle end of the corresponding water transfer member 2. Both of the first and second electrodes (3, 4) can be made of a metal material such as stainless steels or a synthetic resin containing an electric conductive material such as carbon.

Figure 2:
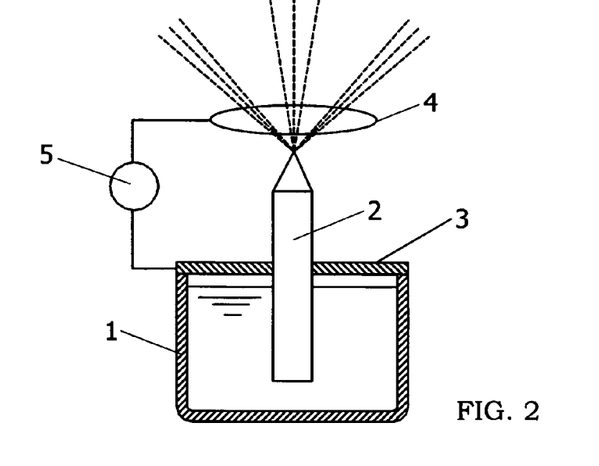
FIG. 2 is a schematic diagram illustrating the principle of generating the charged fine particulate water.
Figure 3A:
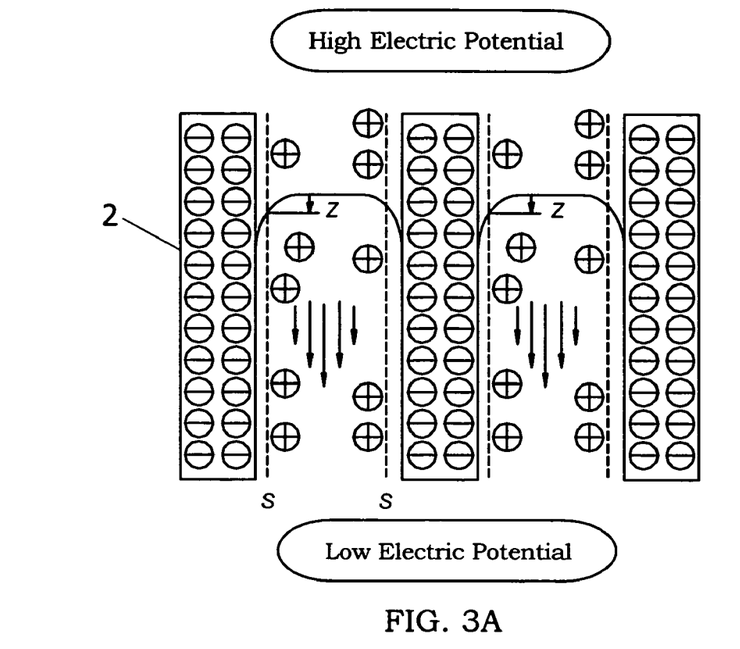
FIGS. 3A and 3B are explanatory diagrams illustrating the movement of electric charges in a water transfer member.
Figure 3B:
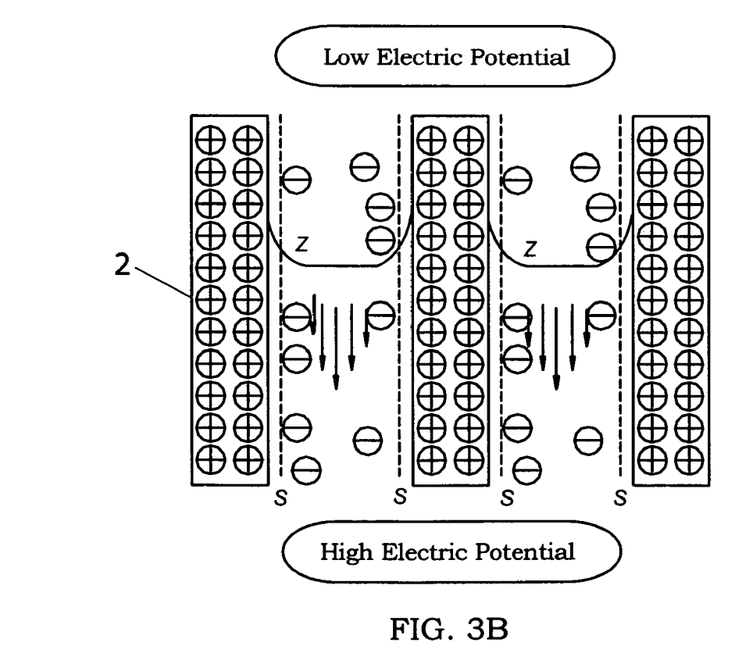

The principle of generating the charged fine particulate water by use of this electrostatic atomizer is shown in FIG. 2. Water in the water tank 1 is transferred from the bottom ends of the water transfer members 2 of the porous material towards the needle ends by the capillary phenomenon. As the water used as a raw material of the charged fine particulate water, for example, it is possible to use running water, underground water, electrolytic water, pH regulated water, mineral water, water containing valuable components such as vitamin C and amino acids, or water containing aroma oil, aromatic substance or a deodorizer. By applying the high voltage between the first electrode 3 and the second electrodes 4 by the voltage applying unit 5 in the state of supplying water to the top ends of the water transfer members 2 by the capillary phenomenon, the water transferred to the top ends of the water transfer members 2 undergoes Rayleigh fission, so that atomization is achieved. In the present embodiment, when the electric-field intensity applied between the first electrode 3 and the second electrode 4 is in a range of 700 to 1200 V/mm, it is possible to obtain the mist of the charged fine particulate water having the nanometer particle size of 3 to 100 nm and containing the radicals such as hydroxyl radicals and superoxides.

By controlling the kind of the porous material used as the water transfer member 2, the shape of the water transfer member 2, the distance between the water transfer members 2 and the second electrode 4, the voltage value or the current value applied between the first and second electrodes (3, 4), it is possible to obtain the charged fine particulate water having a desired nanometer particle size. For example, when the electric-field intensity of 700 to 1200 V/mm is applied, the mist having the particle size of 3 to 20 nm and the mist having the particle size of 30 to 50 nm are mainly generated. On the other hand, when the electric-field intensity of 900 V/mm is applied, the mist of the charged fine particulate water having a uniform particle size of 16 to 20 nm can be obtained.

The thus obtained charged fine particulate water is characterized by having the nanometer particle size. In the present specification, the "nanometer" size means the particle size not greater than 1 micron. Since the particle size is greater than 1 micron, the diffusion property deteriorates. As a result, it is substantially impossible to uniformly disperse the mist of the charged fine particulate water in every corner of a desired space. In addition, it becomes difficult to sufficiently achieve the deodorizing effect and the effect of inactivating bacteria and allergens due to a reduction in amounts of active species and electric charges contained in the charged fine particulate water.

A more preferable particle size of the charged fine particulate water of the present invention is in a range of 3 to 100 nm (electrical mobility is in a range of 0.1 to 0.001 $cm^2/vsec$). When the particle size is less than 3 nm, it may become difficult to uniformly provide the effects of the charged fine particulate water in the desired space due to a reduction in lifetime of the radicals contained in the charged fine particulate water. In particular, when diffusing the charged fine particulate water into a space having an obstacle therein, it becomes difficult to disperse the charged fine particulate water in every corner of the space. On the other hand, when the particle size exceeds 100 nm, the charged fine particulate water is hard to infiltrate into clearances of the skin's horny layer, which are presumed to be approximately in a range of 70 to 100 nm. As a result, it may difficult to improve the moisture retention of the skin.

Secondly, the charged fine particulate water of the present invention is characterized by containing the radicals. The kind of the radical is not limited. For example, it is preferred that the radicals comprise hydroxyl radicals, superoxides, nitrogen monoxide radicals and oxygen radicals. These radicals possess a high reactivity, and it is not needed to use a raw material for generating the radicals because they can be generated from oxygen or water vapor in the air. Thus, it is possible to stably generate the charged fine particulate water containing the radicals.

The polarity of the charged fine particulate water of the present invention is not limited. When it is negatively charged, it is possible to provide a stress relaxation effect that is known as a so-called minus-ion effect as well as the deodorizing effect. In addition, when the first electrode 3 is the negative electrode, and the second electrode 4 is the ground electrode, it is possible to supply the mist of the negatively-charged fine particulate water into the desired space through the opening 40 of the second electrode 4.

The charged fine particulate water may contain acidic active species in addition to the radicals. In this case, it is possible to more effectively deodorize typical bad-odor components, i.e., alkaline odor components such as amine compounds. The kind of the acidic active species is not limited. For example, since nitrogen oxides or organic acids are generated by use of nitrogen and carbon dioxide in the air, the charged fine particulate water containing the acidic active species can be stably obtained without adding the raw material therefore.

In addition, the charged fine particulate water may contain at least one of nitric acid, nitric acid hydrate, nitrous acid and nitrous acid hydrate. In this case, by keeping the charged fine particulate water in a slightly acidic condition, it is possible to easily obtain the effect of infiltrating the charged fine particulate water into the skin and the moisture retention effect as well as the effect of deodorizing the alkaline odor components.

To create an environment where the mist of the charged fine particulate water of the present invention generated by the above-described device is dispersed in a desired space, it is preferred to supply the mist at a proportion of 0.1 g/hr or more, and particularly 0.5 g/hr or more. The mist supply amount can be measured according to the reduced amount of water in the water tank 1 of the electrostatic atomizer.

By the way, when the first electrode 3 is grounded, and a negative voltage is applied to the second electrode 4 to generate the charged fine particulate water, it is preferred that the water transfer member 2 is made of a material having an isoelectric point, which is negatively charged by the pH value of water supplied from the water tank 1. That is, when mineral components such as Ca and Mg are contained in the water used as the raw material of the charged fine particulate water, they are transferred to the top ends of the water transfer members 2 by the capillary phenomenon, and then reacted with carbon dioxide in the air, so that precipitations such as $CaCO_3$ and MgO are generated at the top ends of the water transfer members 2. These precipitations prevent the electrostatic atomization, i.e., the generation of the charged fine particulate water.

By selecting the porous ceramic material in consideration of the pH value of the water used, it is possible to prevent the flow of Mg ions and Ca ions dispersed in the water toward the needle ends of the water transfer members 2 by use of an electroosmotic flow caused in the capillaries of the porous material.

FIG. 3A is a schematic diagram illustrating the eletroosmotic flow caused when the negatively-charged fine particulate water is generated by using the water transfer member 2 of the material having the pH value at the isoelectric point lower than the pH value of the water used. For example, when the water transfer member 2 is made of porous silica, silanol group is alienated by the contact between the porous silica and water, so that inner walls of the capillaries of the porous silica are negatively charged, and a positive-charge immobile layer is formed at the surfaces. In addition, a positive-charge diffusion layer is formed on the immobile layer, thereby obtaining an electric double layer. In the figure, a "S" designates a slip surface in the electric double layer, and "Z" designates a zeta potential. Under this condition, for example, when the electric field is applied such that the first electrode 3 is the negative electrode and the second electrode 4 is the positive electrode, the electroosmotic flow is generated in a direction toward the negative electrode, as shown by the arrows in FIG. 3A, so that Mg ions and Ca ions contained in the water are transferred in a direction away from the needle end of the water transfer member 2. Therefore, it is possible to transfer the water toward the needle ends of the water transfer members 2 by the capillary phenomenon, while preventing that the Mg ions and the Ca ions are transferred toward the needle ends.

FIG. 3B is a schematic diagram illustrating the eletroosmotic flow caused when the positively-charged fine particulate water is generated by using the water transfer member 2 of the material having the pH value at the isoelectric point higher than the pH value of the water used. For example, when the water transfer member 2 is made of porous magnesia, inner walls of the capillaries of the porous magnesia are positively charged by the contact between the porous magnesia and water, and a negative-charge immobile layer is formed at the surfaces. In addition, a negative-charge diffusion layer is formed on the immobile layer, thereby obtaining an electric double layer. Under this condition, for example, when the electric field is applied such that the first electrode 3 is the positive electrode and the second electrode 4 is the ground electrode, the electroosmotic flow is generated in a direction toward the positive electrode, as shown by the arrows in FIG. 3B, so that Mg ions and Ca ions contained in the water are transferred in a direction away from the needle end of the water transfer member 2. Therefore, it is possible to transfer the water toward the needle ends of the water transfer members 2 by the capillary phenomenon, while preventing that the Mg ions and Ca ions are transferred toward the needle ends.

From the above reasons, when the water used has a pH value greater than 10, the ceramic material having a pH value of not greater than 10 at the isoelectric point is used. When the pH value of the water is in a range of 7 to 10, the ceramic material having a pH value smaller than 7 at the isoelectric point is used. Table 1 shows pH values at the isoelectric point of porous ceramic materials.

TABLE 1

| Ceramic material | pH value at isoelectric point |
|---|---|
| Silica | 1~2 |
| Zirconia | 4 |
| Titania | 5~7 |
| Alumina | 7~9 |
| Magnesia | 12 |

EXAMPLES

A mist of charged fine particulate water was generated by use of the apparatus shown in FIG. 1A. As the conditions of generating the charged fine particulate water, the first electrode 3 is the negative electrode, the water transfer member 2 is made of a porous material having a porosity of 40%, and a grain size of 3 μm, and a diameter of the needle end of the water transfer member is ϕ0.25 mm. The electric-field intensity applied between the electrodes is 900 V/mm. By measuring the reduced amount of water in the water tank 1, the generation amount of the charged fine particulate water in this Example is 0.5 g/hr. In addition, since the second electrode 4 is the ground electrode, the polarity of the charged fine particulate water provided from the opening 40 is negative.

The particle size of the charged fine particulate water was determined by measuring electrical mobility by use of a differential electrical mobility analyzer (DMA/Wyckoff. Co., Ltd), and then converting the electrical mobility into the particle size according to the Stokes' law. In this case, it is possible to accurately measure the particle size of the charged fine particulate water, and control the operating conditions of the electrostatic atomizer in a feedback manner according to the determined particle size. As a result, the charged fine particulate water having a desired nanometer particle size can be generated. For example, after the electrical mobility of the charged fine particulate water is measured, and the particle size of the charged fine particulate water is estimated by converting the electrical mobility into the particle size according to the Stokes' law, the electric-field intensity to be applied between the electrodes may be finely controlled according to the estimated value of the particle size in order to generate the charged fine particulate water having the desired particle size.

Figure 4:
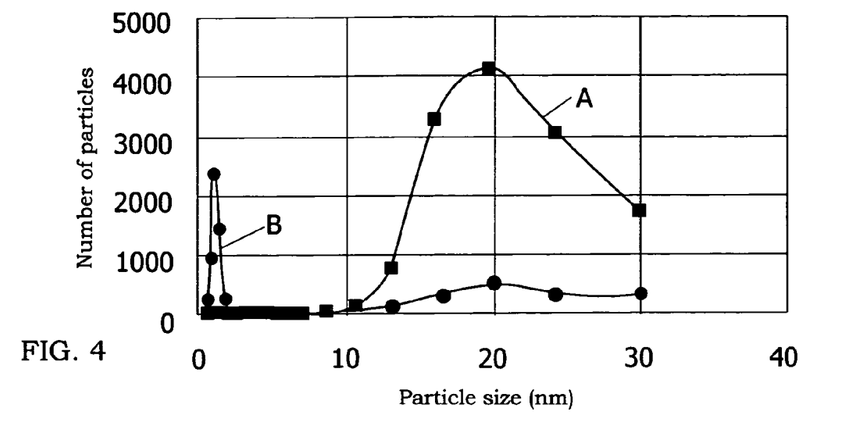
FIG. 4 is a graph showing a particle-size distribution of the charged fine particulate water.
Figure 5:
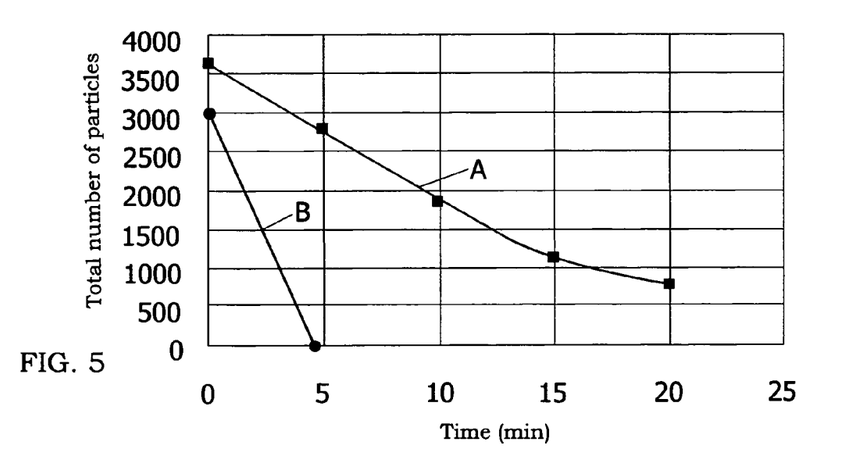
FIG. 5 is a graph showing a change with respect to time of the number of particles of the charged fine particulate water.

FIG. 4 shows measurement results of the particle size. In FIG. 4, "A" designates a particle-size distribution of the charged fine particulate water of this Example. From this results, it can be understood that the charged fine particulate water of this Example has a relatively narrow distribution of 10 to 30 nm around a peak at the vicinity of 20 nm. In FIG. 4, "B" designates a particle-size distribution of minus ions generated by use of electrodes for corona discharge. This result shows that the number of particles (molecules) having the particle size of approximately 1 nm is much greater than the number of particles (molecules) having the particle size of 10 to 30 nm. In addition, FIG. 5 shows changes with respect to time of the number of particles of the charged fine particulate water "A" and the number of particles of the minus ions "B" of FIG. 4. From this graph, it can be understood that the lifetime of the charged fine particulate water "A" having the particle size of 10 to 30 nm is 4 times longer or more than the lifetime of the minus ions "B".

Figure 6:
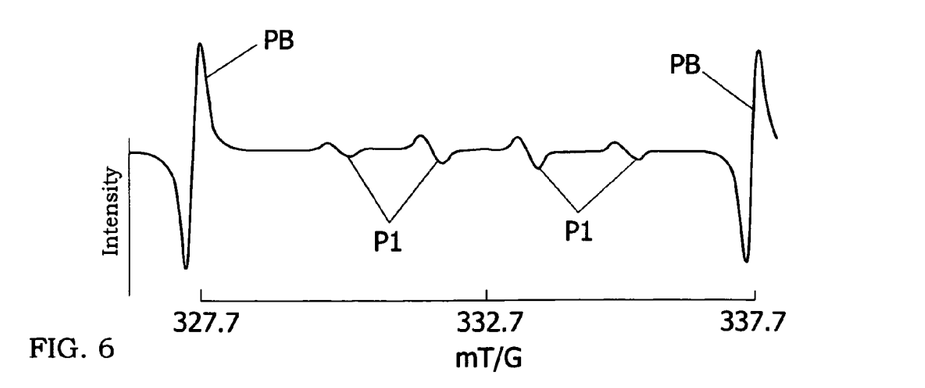
FIG. 6 is an Electron Spin Resonance (ESR) spectrum chart of radicals in the charged fine particulate water.

The radicals contained in the charged fine particulate water can be measured by introducing the charged fine particulate water into a solution containing a spin trapping agent to stabilize the radicals, and then using electron spin resonance (ESR) spectroscopy. FIG. 6 shows a result of measuring the radicals in the charged fine particulate water "A" by the ESR spectroscopy. In FIG. 6, "P1" is a detected peak of the radicals, and "PB" is a peak of manganese oxide used as the reference material. From these results, it can be confirmed that the charged fine particulate water of this Example is negatively charged, has the particle size of 10 to 30 nm, and contains the radicals.

Figure 7:
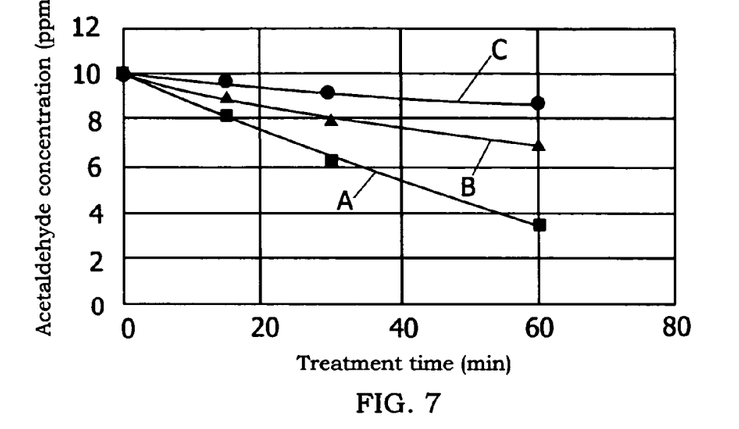
FIG. 7 is a graph showing measurement results of the acetaldehyde decomposing capability of the charged fine particulate water.

As an example, a deodorizing effect of the charged fine particulate water containing the radicals is introduced below. This deodorizing effect is achieved by a chemical reaction between an odor gas and the radicals in the charged fine particulate water. The followings are reaction formulas between the radicals and various kinds of odor gases, typified by acetaldehyde. ".OH" designates a hydroxy radical.

acetaldehyde: $CH_3CHO + 6 \cdot OH + O_2 \rightarrow 2CO_2 + 5H_2O$
ammonia: $2NH_3 + 6 \cdot OH \rightarrow N_2 + 6H_2O$
acetic acid: $CH_3COOH + 4 \cdot OH + O_2 \rightarrow 2CO_2 + 4H_2O$
methane gas: $CH_4 + 4 \cdot OH + O_2 \rightarrow CO_2 + H_2O$
carbon monoxide: $CO + 2 \cdot OH \rightarrow CO_2 + 4H_2O$
nitrogen monoxide: $2NO + 4 \cdot OH \rightarrow N_2 + 2O_2 + 2H_2O$
formaldehyde: $HCHO + 4 \cdot OH \rightarrow CO_2 + 3H_2O$ FIG. 7 shows a result of treating 10 ppm of acetaldehyde in a chamber having an internal volume of 3 liters with the charged fine particulate water of this Example for 1 hour. In FIG. 7, "A" shows the deodorizing effect of the charged fine particulate water of this Example. In this case, the acetaldehyde concentration was reduced to 40% of the acetaldehyde concentration measured at the time of starting the measurement by the treatment for 60 minutes. In FIG. 7, "B" designates the case of performing the treatment with the minus ions having the particle size of 1 nm and generated by use of the electrodes for corona discharge, and "C" designates the case of not performing the treatment.

In addition, a mold fungus was exposed to the charged fine particulate water of this Example. In this case, the survival rate of the mold fungus became zero after the exposure for 60 minutes. It is believed that the OH radical has the effect of decomposing the fungal-thread of the mold fungus.

Figure 8:
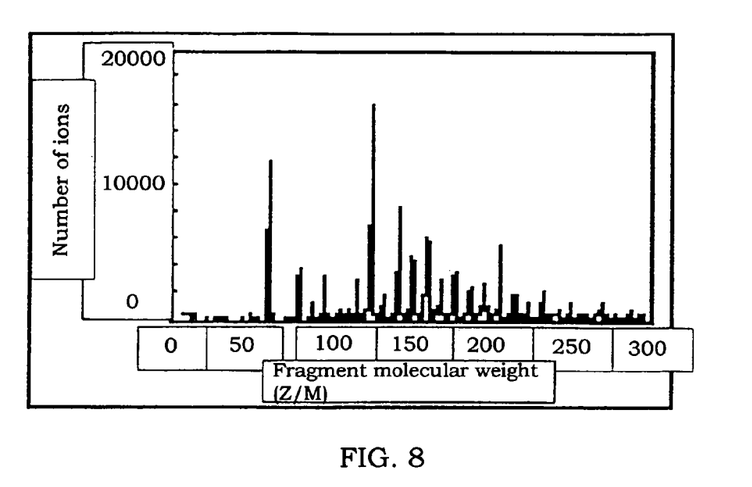
FIG. 8 is a mass spectrum chart of the charged fine particulate water.

Acidic active species contained in the charged fine particulate water were measured by means of a drift tube ion mobility/mass spectroscopy. Results are shown in FIG. 8 and TABLE 2. The acidic active species contained in the charged fine particulate water can be also measured by introducing the charged fine particulate water in purified water, and then using ion chromatography.

TABLE 2

| Molecular weight | Chemical formula | The number of ions |
|---|---|---|
| 46 | $NO_2$— | 33 |
| 62 | $NO_3$— | 11669 |
| 80 | $NO_3$—$(H_2O)$ | 3677 |
| 89 | COOHHCOO— | 1291 |
| 98 | $NO_3$—$(H_2O)_2$ | 3383 |
| 107 | COOHHCOO—$(H_2O)$ | 654 |
| 108 | $NO_2NO_3$— | 229 |
| 116 | $NO_3$—$(H_2O)_3$ | 3072 |
| 124 | $NO_3NO_3$— | 8858 |
| 125 | $HNO_3NO_3$ | 15836 |
| 134 | $NO_3$—$(H_2O)_4$ | 1847 |
| 142 | $NO_3NO_3$—$(H_2O)$ | 3448 |
| 143 | $HNO_3NO_3$—$(H_2O)$ | 8335 |
| 152 | $NO_3$—$(H_2O)_5$ | 4837 |
| 160 | $NO_3NO_3$—$(H_2O)_2$ | 3138 |
| 161 | $HNO_3NO_3$—$(H_2O)_2$ | 6014 |
| 170 | $NO_3$—$(H_2O)_6$ | 2059 |
| 178 | $NO_3NO_3$—$(H_2O)_3$ | 1589 |
| 179 | $HNO_3NO_3$—$(H_2O)_3$ | 3399 |
| 187 | ? | 1847 |
| 188 | $NO_3$—$(H_2O)_7$ | 1879 |
| 196 | $NO_3NO_3$—$(H_2O)_4$ | 850 |
| 197 | $HNO_3NO_3$—$(H_2O)_4$ | 2272 |
| 206 | $NO_3$—$(H_2O)_8$ | 5491 |
| 214 | $NO_3NO_3$—$(H_2O)_5$ | 735 |
| 215 | $HNO_3NO_3$—$(H_2O)_5$ | 1487 |
| 224 | $NO_3$—$(H_2O)_9$ | 1144 |
| 232 | $NO_3NO_3$—$(H_2O)_6$ | 833 |
| 233 | $HNO_3NO_3$—$(H_2O)_6$ | 1683 |
| 242 | $NO_3$—$(H_2O)_{10}$ | 507 |
| 250 | $NO_3NO_3$—$(H_2O)_7$ | 719 |
| 251 | $HNO_3NO_3$—$(H_2O)_7$ | 1144 |
| 268 | $NO_3NO_3$—$(H_2O)_8$ | 605 |
| 269 | $HNO_3NO_3$—$(H_2O)_8$ | 1373 |
| 286 | $NO_3NO_3$—$(H_2O)_9$ | 507 |
| 287 | $HNO_3NO_3$—$(H_2O)_9$ | 768 |

The measurement results show that the charged fine particulate water of this Example contains various kinds of acidic active species such as nitrogen oxides and organic acids, which are presumed to be generated by use of nitrogen and carbon dioxide in the air.

Figure 9:
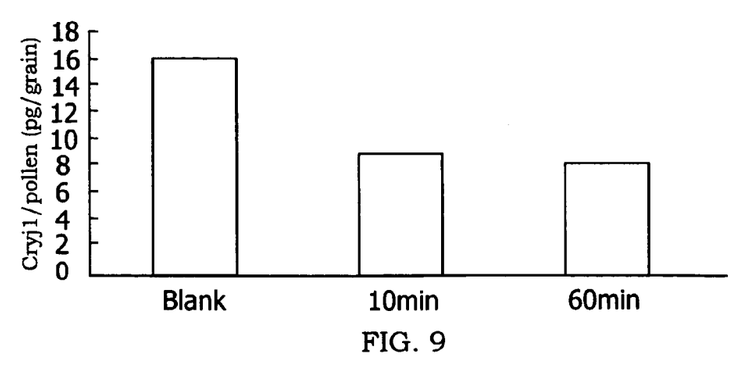
FIG. 9 is a graph showing results of an ELISA test for evaluating the capability of inactivating cedar pollen antigen of the charged fine particulate water.

In addition, FIG. 9 shows a result of performing an ELISA test by exposing antigen Cry j1 extracted from cedar pollen allergy to the charged fine particulate water of this Example. After the elapse of 10 minutes, the antigen amount was reduced to a half of the antigen amount measured at the initial (blank) state. In this test, when the particle size is smaller than 3 nm, or larger than 50 nm, such a remarkable antigen-inactivation effect could not be obtained. In addition, the charged fine particulate water having the extremely fine particle size of 3 to 50 nm had little effect on moisture control in the air.

An antiviral effect of the charged fine particulate water of this Example was evaluated by preparing in a cylindrical vessel (φ55×200 mm), in which the charged fine particulate water generated by the electrostatic atomizer of FIG. 1 is dispersed, spraying a virus solution in the cylindrical vessel from its one end opening, collecting the virus from the opposite end opening of the cylindrical vessel by use of an impinger, and then using the plaque method. As a result, the plaque number in the collected solution was much smaller than the case of simply exposing the virus solution to the minus ions.

Moreover, *Escherichia coli* O157 was exposed to the charged fine particulate water of this Example. After the elapse of 30 minutes, the inactivation ratio reached 100%. It is believed that the active species in the charged fine particulate water denatures the protein of the bacteria's surface to prevent the propagation of the bacteria.

Figure 10:
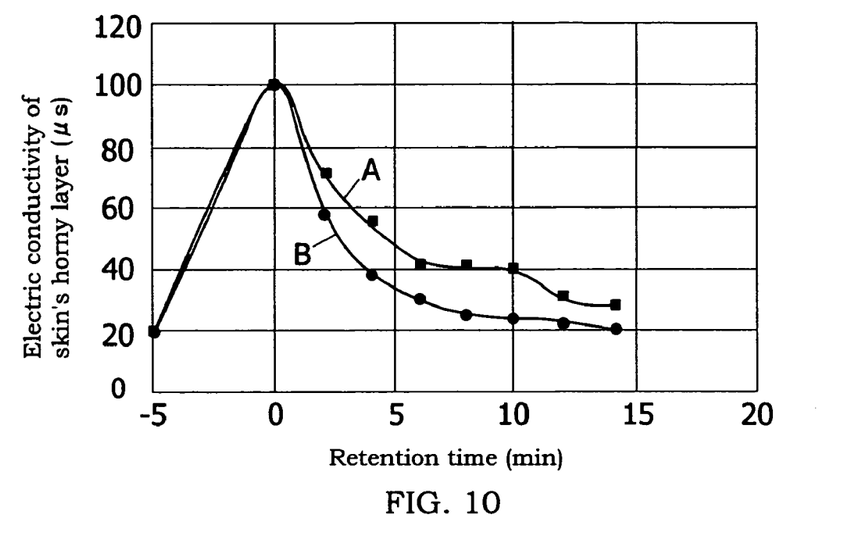
FIG. 10 is a graph showing a change in electrical conductivity of the skin's horny layer exposed to cold water and then the charged fine particulate water.

FIG. 10 shows results of evaluating a moisture content in the skin after directly exposing the skin to the charged fine particulate water of this Example. In FIG. 10, "A" designates the case of using the charged fine particulate water, and "B" designates the case of using the minus ions having the particle size of 1 nm and generated by use of the electrodes for corona discharge. From these results, it can be understood that the moisture retention is maintained for an extended time period by use of the charged fine particulate water of this Example.

Figure 11:
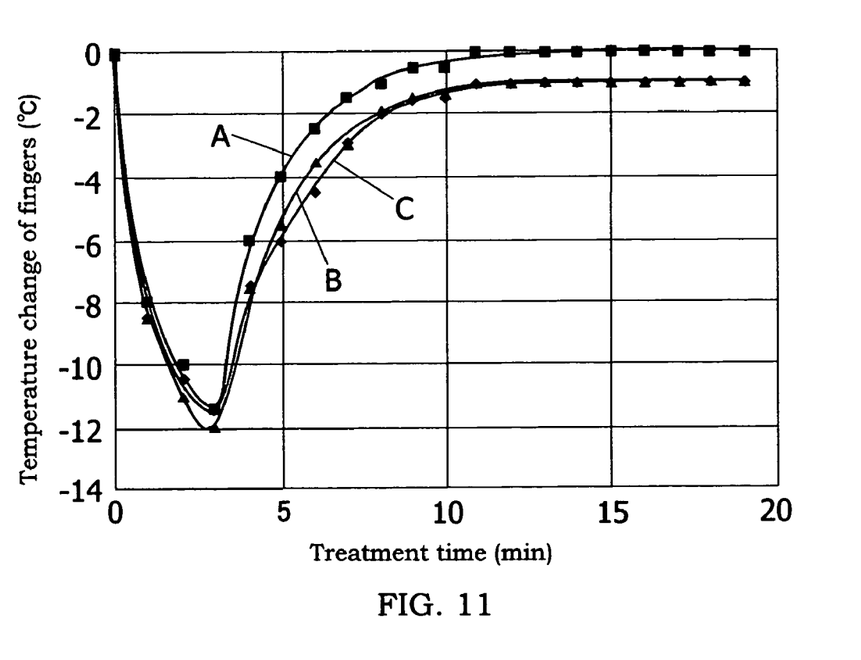
FIG. 11 is a graph showing a change in temperature of fingers exposed to the cold water and then the charged fine particulate water.

After fingers cooled by cold water were exposed to the negatively-charged fine particulate water of this Example, a change with respect to time of the body temperature was measured. Results are shown in FIG. 11. In FIG. 11, "A" designates the case of using the charged fine particulate water, "B" designates the case of using the minus ions having the particle size of 1 nm, and "C" designates the case of not using the charged fine particulate water or the minus ions. From these results, it can be understood that the use of the charged fine particulate water is more effective to facilitate increasing the body temperature, as compared with the case of using the minus ions.

From these results, it is confirmed that the charged fine particulate water having the nanometer particle size are excellent in deodorizing, inactivating the substance causing pollen allergen, inactivating the virus or the bacteria in the air, removing the mold fungus in the air, and mildew proofing.

INDUSTRIAL APPLICABILITY

As described above, since the charged fine particulate water contains the radicals and have a nanometer particle size, it exhibits a remarkably-improved diffusion property into a space, as compared with the conventional charged fine particulate water having a micrometer particle size. Therefore, the charged fine particulate water can come in a very narrow space, so that the radicals effectively decompose/deodorize the bad-odor components, and inactivate bacteria, mold funguses, viruses and allergens such as pollen.

In addition, according to the present invention, it is possible to create an indoor environment where the charged fine particulate water containing the radicals are uniformly dispersed, which can not be achieved by use of the short-lived, charged particles having the micrometer particle size. Therefore, the present invention is useful to provide comfortable dwelling and working spaces.

The invention claimed is:

1. Rayleigh fission generated charged fine particulate water having a particle size of 3 to 100 nm and containing at least one of hydroxyl radicals, superoxides, nitrogen monoxide radicals and oxygen radicals, wherein the charged fine particulate water is generated by Rayleigh fission caused by applying a high voltage to water on a needle end.

2. The charged fine particulate water as set forth in claim 1, containing acidic chemical species.

3. The charged fine particulate water as set forth in claim 2, containing a nitrogen oxide or an organic acid.

4. The charged fine particulate water as set forth in claim 1, containing at least one of nitric acid, nitric acid hydrate, nitrous acid and nitrous acid hydrate.

5. The charged fine particulate water as set forth in claim 1, wherein the charged fine particulate water is negatively charged.

6. A method of creating an environment where a mist of charged fine particulate water is dispersed, said method comprising the steps of: providing a pair of electrodes, water supply unit configured to supply water between said electrodes, and a voltage applying unit configured to apply a voltage between said electrodes; generating said mist of charged fine particulate water having a particle size of 3 to 100 nm and containing at least one of hydroxyl radicals, superoxides, nitrogen monoxide radicals and oxygen radicals, wherein the charged fine particulate water is generated by Rayleigh fission caused by applying a high voltage between said electrodes, while supplying water between said electrodes by said water supply unit; and supplying said mist into a desired space to create the environment where said mist of charged fine particulate water is dispersed in the desired space.

* * * * *